(12) United States Patent
Shihata

(10) Patent No.: US 8,795,248 B2
(45) Date of Patent: Aug. 5, 2014

(54) DEVICE AND METHOD FOR MENSTRUAL BLOOD COLLECTION

(76) Inventor: Alfred A. Shihata, Del Mar, CA (US)

( * ) Notice: Subject to any disclaimer, the term of this patent is extended or adjusted under 35 U.S.C. 154(b) by 0 days.

(21) Appl. No.: 13/457,284

(22) Filed: Apr. 26, 2012

(65) Prior Publication Data

US 2013/0110060 A1   May 2, 2013

Related U.S. Application Data

(60) Provisional application No. 61/553,741, filed on Oct. 31, 2011.

(51) Int. Cl.
*A61F 13/15* (2006.01)
*A61F 13/20* (2006.01)
*A61F 5/455* (2006.01)

(52) U.S. Cl.
CPC .................................... *A61F 5/4553* (2013.01)
USPC ................. 604/385.17; 604/328; 604/385.18; 604/327

(58) Field of Classification Search
CPC ...... B65D 1/02; B65D 1/0223; B65D 1/0238; B65D 1/0246; B65D 1/023; B65D 1/22; B65D 3/06; B65D 3/20; B65D 3/04; B65D 3/02; B65D 5/0085; B65D 77/006; B65D 5/0245; B65D 5/06; B65D 5/01; B65D 2583/0404; B65D 2583/045; B65D 2583/0463; B65D 75/5855; B65D 83/0481; A61F 13/2048; A61F 6/08; A61F 5/4553; C12Q 1/42; C12Q 1/6886
USPC ................. 604/354, 330, 327–328; D24/141; 222/424.5, 425, 454
See application file for complete search history.

(56) References Cited

U.S. PATENT DOCUMENTS

| | | | |
|---|---|---|---|
| 71,414 A | 11/1867 | Rohleder | |
| 1,190,612 A * | 7/1916 | Weil | 222/527 |
| 1,986,504 A | 1/1935 | Cubbon | |
| 1,996,242 A | 4/1935 | Hagedorn | |
| 2,089,113 A | 8/1937 | Chalmers | |
| 2,534,990 A | 12/1950 | Chalmers | |
| 2,616,426 A | 11/1952 | Gordon | |
| 3,093,273 A * | 6/1963 | Borah | 222/527 |
| 3,326,421 A * | 6/1967 | Peace | 222/143 |

(Continued)

OTHER PUBLICATIONS

Hartman, Andrew, Cheers Menstrual Cup, May 23, 2010.*

(Continued)

*Primary Examiner* — Michele M Kidwell
(74) *Attorney, Agent, or Firm* — One3 IP Management, PC; Peter D. Weinstein; Dean G. Stathakis

(57) ABSTRACT

A hemispherical receptacle made of compressible material for menstrual fluid collection is disclosed herein. In a preferred method the receptacle is compressed during insertion. The receptacle further has a resilience for restoring to its original shape after being inserted into the vagina. To facilitate removal, the receptacle includes a pulling ring at a lower end thereof; and a unique flange lid portion is included at an open upper end acting as a funnel to direct the menstrual blood into the receptacle. This unique flange portion is designed with a living hinge that transfers the device from a closed to an open position. In the closed position, the flange portion allows blood to get into the receptacle while preventing it from spilling out. The open position herein is for emptying and cleaning the receptacle.

17 Claims, 4 Drawing Sheets

(56) References Cited

U.S. PATENT DOCUMENTS

| | | | | |
|---|---|---|---|---|
| 3,367,380 A | * | 2/1968 | Dickey | 383/104 |
| 3,404,682 A | | 10/1968 | Waldron | |
| 3,559,847 A | * | 2/1971 | Goodrich | 222/107 |
| 3,768,700 A | * | 10/1973 | Stranicky | 222/107 |
| 3,841,333 A | | 10/1974 | Zalucki | |
| 3,845,766 A | | 11/1974 | Zoller | |
| 3,983,874 A | | 10/1976 | Davis et al. | |
| 4,607,630 A | | 8/1986 | Spits | |
| 4,848,363 A | * | 7/1989 | Cattanach | 128/834 |
| 5,342,331 A | * | 8/1994 | Silber et al. | 604/330 |
| 5,476,455 A | * | 12/1995 | Silber | 604/330 |
| 5,498,252 A | * | 3/1996 | Silber | 604/330 |
| 5,743,893 A | | 4/1998 | Kalb | |
| 5,827,248 A | | 10/1998 | Crawford | |
| 5,885,265 A | | 3/1999 | Osborn, III et al. | |
| 5,947,991 A | * | 9/1999 | Cowan | 606/191 |
| D426,410 S | * | 6/2000 | De Laforcade | D6/512 |
| D436,539 S | * | 1/2001 | Spreitzer et al. | D9/503 |
| 6,332,878 B1 | | 12/2001 | Wray et al. | |
| D482,493 S | * | 11/2003 | Lillelund et al. | D28/73 |
| 6,796,973 B1 | * | 9/2004 | Contente et al. | 604/354 |

OTHER PUBLICATIONS http://www.academyart.edu/news/articles/industrial-design-alum-wins-gold-competition.html, Industrial Design Alum Wins Gold in Her First Competition.*

* cited by examiner

DEVICE AND METHOD FOR MENSTRUAL BLOOD COLLECTION

PRIORITY CLAIM

This patent application contains subject matter claiming benefit of the priority date of U.S. Provisional Patent Application Ser. No. 61/553,741 filed on Oct. 31, 2011 and entitled DEVICE AND METHOD FOR MENSTRUAL BLOOD COLLECTION, accordingly, the entire contents of this provisional patent application is hereby expressly incorporated by reference.

BACKGROUND OF THE INVENTION

1. Field of the Invention

The invention generally relates to obstetrical-gynecological devices. More specifically, the present invention, in a preferred embodiment, pertains to intravaginal devices designed to control the collection of menstrual blood and to minimize leaking and spillage of blood from the vagina.

2. Description of the Prior Art

As is known, the vagina is a conduit extending from the woman's cervix to the exterior of the body. The vaginal canal is about 9 or 10 cm long. Its lumen is generally quite small, however, it has great capacity to expand. Menstrual blood passes to the outside through the vaginal canal without the woman's control during periodic menses.

Pads have been known for decades but they are bulky, inconvenient, and need to be changed frequently.

More recently, the inconvenience to women resulting from the occurrence of periodic bleeding during the menstrual period have prompted attempts to control the outflow of menstrual bleeding by employing vaginal tampons. Vaginal tampons are common feminine hygiene product devices made of absorbing material and insertable into the vagina by the female user. Due to their absorbing material, tampons, once inserted into the vagina, begin to absorb the blood, which outflows from the cervix into the vagina. The tampons further serve as reservoirs aimed at delaying exit of the blood from the vaginal orifice until they become saturated with blood.

As a limitation, no known tampon is capable of entirely preventing leakage of blood from the vaginal orifice, regardless of shape, size, or absorbency capabilities of the material of which they are made. Blood may leak from the vaginal orifice because the tampon is saturated with blood or because the blood flow is disproportionately heavy for the absorbency capabilities of the inserted tampon. Additionally leakage may result because the tampon does not provide an adequate sealing with the vaginal walls, or orifice or for all the above reasons variously combined.

Various prior art innovations deals with the problem of leakage of menstrual blood through the tampons, for example, by providing additional blood reservoirs to the tampons. Others seek to prevent leakage by increasing the tampons absorbing capabilities by the means of improved absorbing material. Still others employ absorbing pads to apply to the vaginal orifice to capture the blood escaped from the tampon. No known device has been disclosed to provide means of entirely preventing leakage of menstrual blood.

Another group of menstrual hygiene devices introduced for the purpose of avoiding leakage of menstrual blood are the menstrual cups. Menstrual cups are not new in the art of feminine hygiene. U.S. Pat. No. 3,845,766 to Zoller, U.S. Pat. No. 3,626,942 to Waldron, U.S. Pat. No. 2,534,900 to Chalmers and U.S. Pat. No. 5,295,984 to Audrey all disclose a cup shaped menstrual collector made of flexible material impervious to fluid inserted into the vaginal canal for the purpose of collecting menstrual blood and preventing leakage of blood form the vaginal orifice. However, all these devices all suffer from poor ergonomic design. Specifically, they are all difficult to insert and remove. Regardless of the individual differences among the menstrual blood collector cups, the general design of all these devices makes their insertion into the vaginal canal an uncomfortable and difficult task. Removal of these devices is even more difficult and uncomfortable for the user than the insertion. Further, removal of these devices also pose health and safety issues. Particularly, women often struggle to remove these devices by inserting their fingers deep into the vagina, which can lead to finger nail abrasions. Such manual removal of the device risks physically injuring the interior of the vagina by fingernail scratching or tearing. Furthermore spillage of blood upon their removal is a very frequent occurrence. Indeed none of the menstrual cups is provided with an effective simple sealable closure apparatus of the cup opening apt to prevent spillage of blood.

In more recent years, there has been a renewed interest in the use of the menstrual cups in lieu of the napkin and the tampon. The menstrual cup is ideally comprised of soft material and is further reusable and convenient. However, menstrual cups have never gained acceptability among women due to difficulty of insertion and removal, and further due to leakage and spillage of blood upon removal.

As stated, conventional menstrual cups have been known for some time. A early example was proposed by Hagedorn, U.S. Pat. No. 1,996,242, entitled "Catamenial Receptacle." Yet another example was proposed by Chalmers, U.S. Pat. No. 2,089,113, entitled "Catamenial Appliance." Still another example was proposed by Crawford entitled "Menstrual Cup", U.S. Pat. No. 5,827,248. Generally, all these named solutions use a cup to be inserted into the vagina for receiving menstrual blood.

Presently, menstrual cups have not achieved widespread acceptance from women due to certain factors that discourage some potential users. Initially, removal of the menstrual cup from the vagina should be accomplished on a regular basis for emptying, cleaning and hygienic purposes. This is inconvenient to the user. It is not convenient for the user to clean the menstrual cup immediately. This may cause hygienic problems or blood leakage. Additionally, a user may be embarrassed by having to clean the menstrual cup at the sink of a public lavatory. These are perhaps some reasons that the menstrual cup is not generally used.

Therefore, it is an object of the present invention to provide an advanced menstrual collection device that provides better control of untimely leakage of menstrual blood. It is further an object of the present invention to offer a device capable of preventing blood leakage regardless of the anatomical size, shape, changing of direction and of the lumen contour of the vagina. It is an additional object of the present invention to propose a compressible hemispherical device capable of reliably achieving prevention of leakage of menstrual blood while being easy and comfortably inserted and worn.

These, as well as other advantages of the present invention will be more apparent from the following description and drawings. It is understood that changes in the specific structure shown and described may be made within the scope of the claims, without departing from the spirit of the invention.

BRIEF SUMMARY OF THE INVENTION

The present invention specifically addresses and alleviates the above mentioned deficiencies associated with the prior art. The invention is generally an intravaginal compressible hemispherical, or generally spherical shaped main body and flange portion capable of providing reliable vaginal closure to outflow of fluids such as menstrual blood from the vaginal orifice until the woman determines to be the appropriate time for allowing exit of the menstrual blood from the vaginal orifice. Vaginal closure is achieved by the hemispherical main body impermeable to fluids, easily self-adaptable to the variability of sizes and shapes of the vaginal lumen and to the variability of smoothness of the vaginal walls. The compressible hemispherical main body further expands to exert a gentle pressure on the vaginal walls, such a pressure being sufficient to prevent passage of blood between the receptacle member itself and the vaginal walls.

More particularly, the present invention in a first aspect, is receptacle for collecting and retaining menstrual blood, comprising: a generally spherical main body; and a flange portion formed at an upper end of the spherical main body, wherein a flange portion folds about a ring pivot, the flange portion about the ring pivot defining an open position and a closed position to the receptacle, the closed position further being an in use position. In a preferred embodiment, the ring pivot is a living hinge.

The invention in this aspect is additionally characterized wherein the ring pivot is an inner ring, the receptacle further comprising and outer ring, the ring pivot and the outer ring together defining a flat top surface of the receptacle in the in use position. Further, the flange portion and the main body define a fluid capture area even when the receptacle is in the inverted position preventing fluid spill whether the receptacle is inverted or not.

Further, the invention in this aspect is additionally characterized wherein the flange portion further comprises a slope with respect to the main body, the slope acting like a funnel when the receptacle is in the in use position, directing fluid to an interior of the receptacle's main body. The invention is further described wherein when the receptacle is in the open position, the flange portion protrudes outward with respect to the main body portion, and wherein the receptacle is in the in use position, the flange portion protrudes inward with respect to the main body portion. Also, the invention includes a ring handle at a lower end of the receptacle, the ring handle providing for ease of removal using one finger of a user. As stated, the device is provided with a unique sealable lid closure (i.e. flange portion) of the opening of the receptacle to prevent spillage of blood upon removal. The device is further designed to be used as a stand-alone intravaginal device.

In a second aspect, the invention may be characterized as a method for collecting menstrual fluid comprising the steps of: providing a main body of a receptacle made from soft compressible, resilient elastomer material, for example, silicone rubber; providing a flange portion at an upper end thereof; folding the flange portion about a ring pivot at the upper end, the folding defining a receptacle open position and a receptacle closed position; defining a fluid catch area at an interior area of the folding the flange portion about the ring pivot, wherein the closed position is also an in use position; funneling fluid down to the main body in the in use position; and assisting the retention of fluid by the catch area when the receptacle is removed by a user.

The method for collecting menstrual fluid of is additionally characterized in that it comprises removing the receptacle with a ring handle at a lower end of the receptacle. Also the method may be described wherein the receptacle is a first receptacle and further comprising the steps of providing a second receptacle; changing the first receptacle for the second receptacle after a period of about six to twelve hours; and cleaning the first receptacle at a later time as compared to the step of changing the first receptacle.

These, as well as other advantages of the present invention will be more apparent from the following description and drawings. It is understood that changes in the specific structure shown and described may be made within the scope of the claims, without departing from the spirit of the invention.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DETAILED DESCRIPTION OF PREFERRED EMBODIMENTS

Figure 1:
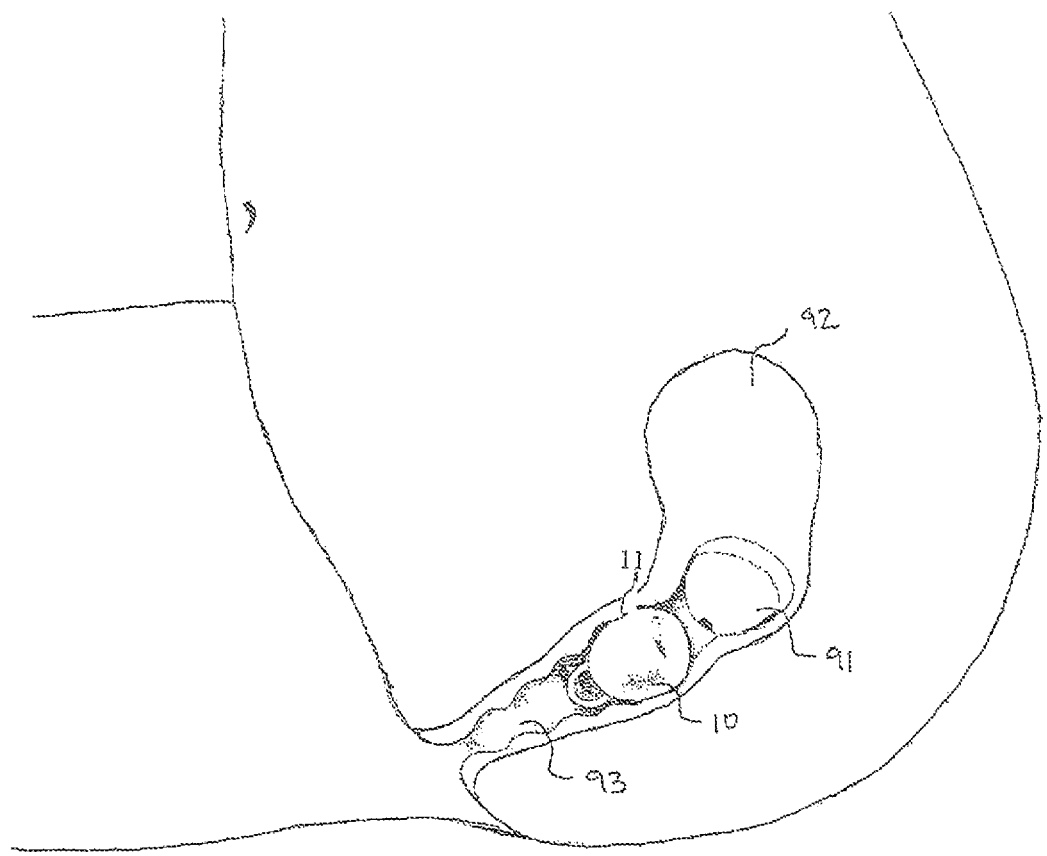
FIG. 1 is an artist's depiction of a first preferred device of the present invention.

With regard to FIG. 1, an overview of a first preferred menstrual fluid receptacle 10 is illustrated. Initially, the receptacle 10 is compressed during insertion. The receptacle 10 further has a resilience for restoring to its original shape after being inserted into the vagina 93 wherein a user's cervix 91 and uterus 92 are shown for illustrative purposes. Also importantly, the compressible hemispherical device 10 has a remarkable adaptability to anatomical size, shape, contour of the vagina 93, to maintain its outer surface in close contact with the vaginal 93 walls and offer a sealing closure to blood in any condition. In position (FIG. 1) the device 10 applies a gentle pressure upon the vaginal 93 walls and adds no discomfort to the female user. Further, the pressure exerted is just barely sufficient to prevent passage of blood between the device 10 and the vaginal 93 walls, such a pressure being generally proportional to the negligible pressure, exerted by menstrual blood.

Figure 2A:
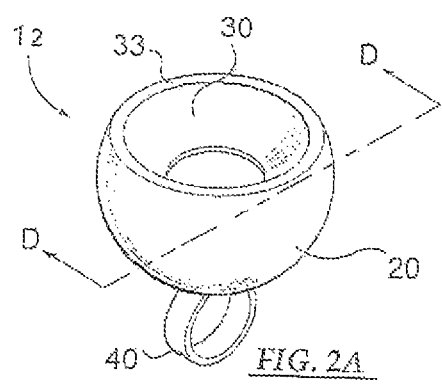
FIG. 2A is a perspective illustration of the device of the present invention in a closed/folded position.
Figure 2B:
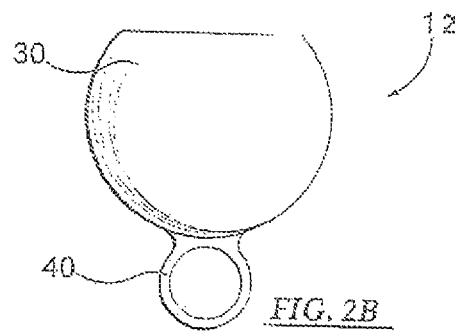
FIG. 2B is a front view thereof.
Figure 2C:
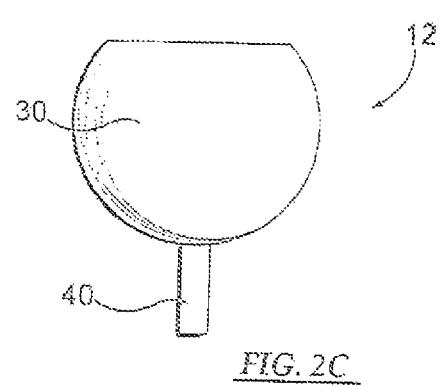
FIG. 2C is a profile view thereof.
Figure 2D:
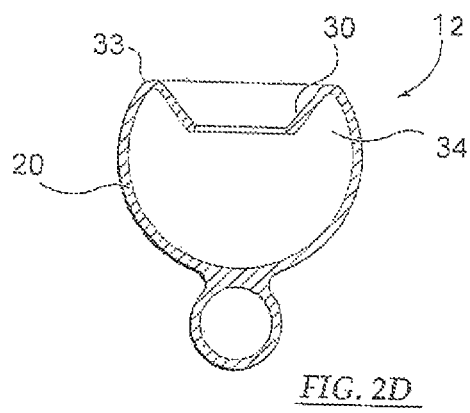
FIG. 2D is a cross sectional view of the device taken along line D-D in FIG. 2A.
Figure 3A:
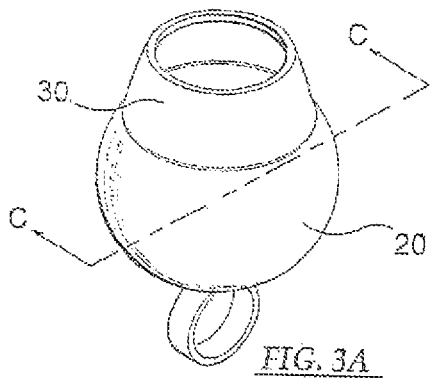
FIG. 3A is a perspective illustration of the device of the present invention in a open/unfolded position.
Figure 3B:
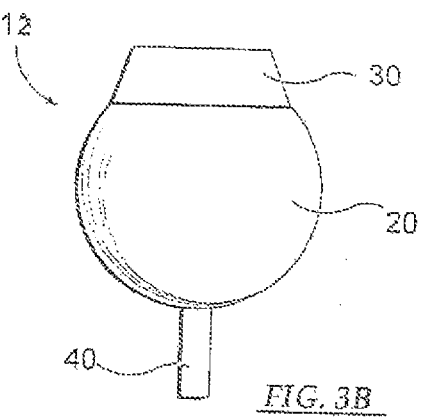
FIG. 3B is a profile view of the device in the open position.
Figure 3C:
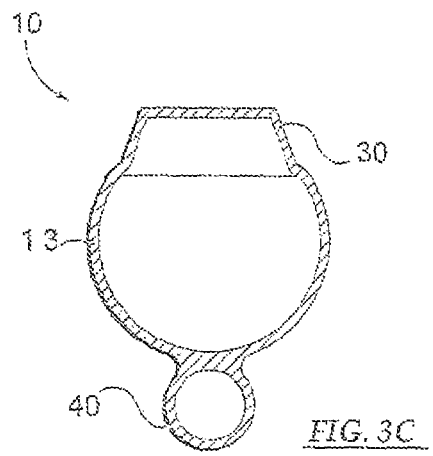
FIG. 3C is a cross sectional view of the device in the open position taken along line C-C in FIG. 2A.
Figure 3D:
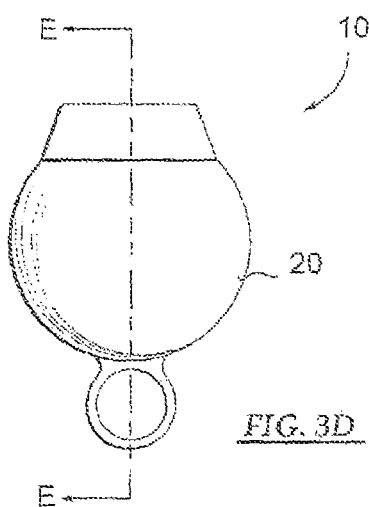
FIG. 3D is a front view thereof.
Figure 3E:
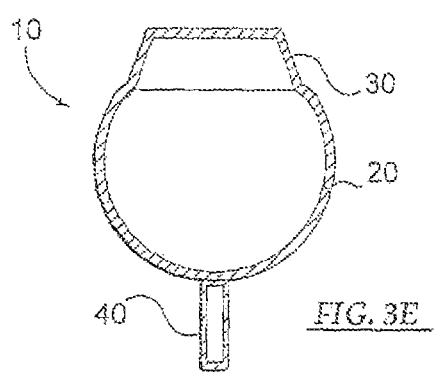
FIG. 3E a cross sectional view of the device in the open position taken along line E-E in FIG. 3D.
Figure 3F:
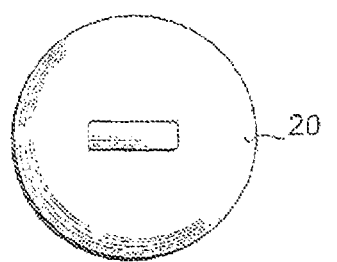
FIG. 3F is a bottom view of the device.
Figure 3G:
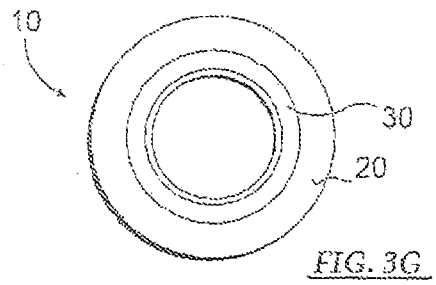
FIG. 3G is a top plan view thereof, specifically in the open position.

With reference to FIG. 2A, a first preferred menstrual fluid receptacle 10 (i.e. cup) is shown in perspective. Initially, it 10 has a generally hemispherical or spherical main body 20. More particularly, its 20 spherical shape is cut off by a plane giving the main body 20 an approximate three-quarter spherical shape. The main body 20 has a primary purpose of retaining menstrual fluid as described in more detail herein.

Figure 5A:
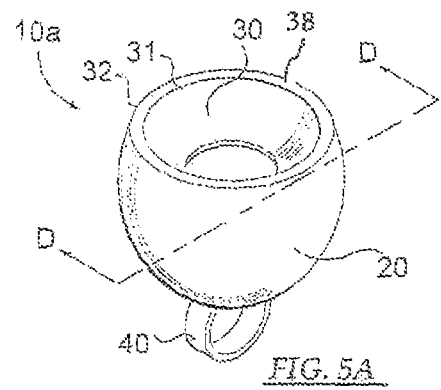
FIG. 5A is a perspective illustration of a second preferred, more elliptical, device in a closed position.
Figure 5B:
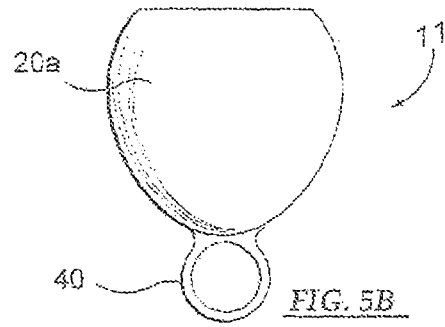
FIG. 5B is a front view thereof.
Figure 5C:
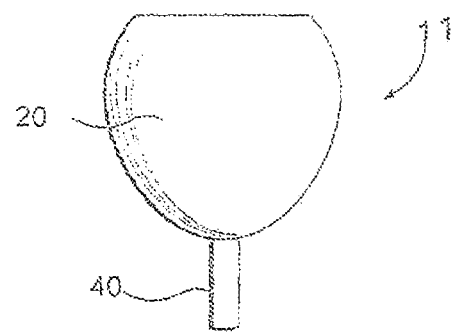
FIG. 5C is a profile view thereof.
Figure 5D:
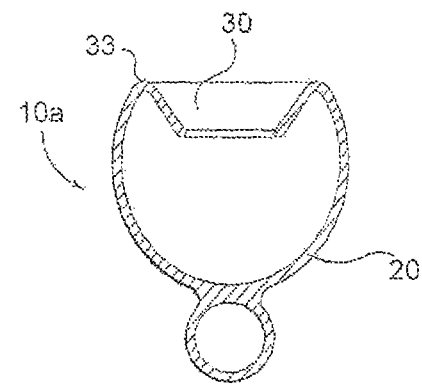
FIG. 5D is a cross sectional view of the second preferred device taken along line D-D in FIG. 5A.
Figure 5E:
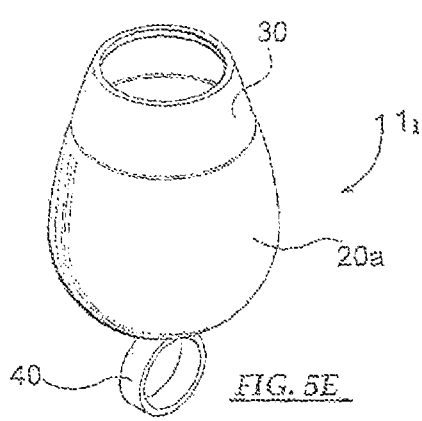
FIG. 5E is a perspective illustration of the second preferred device of the present invention in an open position.
Figure 5F:
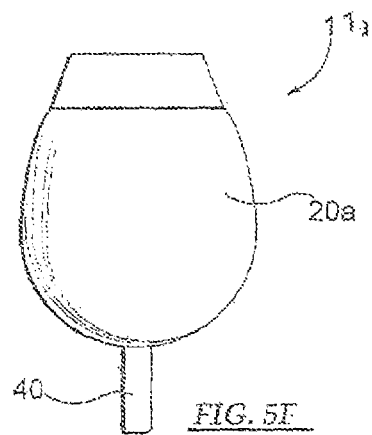
FIG. 5F is a profile view of the second preferred device in the open position.

Taking FIG. 2A through FIG. 2D, along with FIG. 5A through FIG. 5D, the main body 20, 20a may be generally spherical 20, as described above, or generally elliptical or egg shaped 20a as shown in FIG. 5A. through FIG. 5F. A flange lid portion 30 is provided as an extension to the main body 20, 20a about a living hinge 31, 32, 33. More particularly, the living hinge 31, 32, 33 comprises a ring pivot 31 that is essentially a circular hinge formed at an upper end of the spherical main body 20, 20a.

Figure 4:
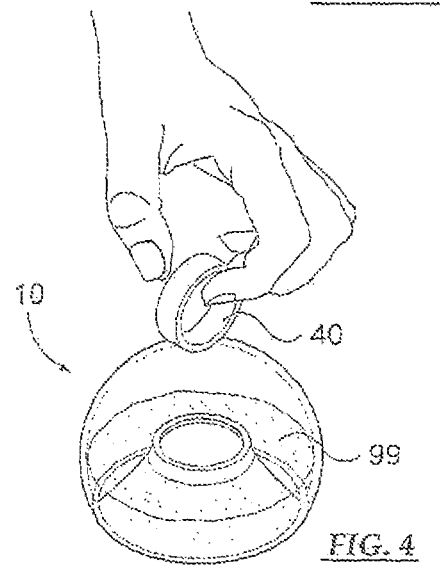
FIG. 4 is an additional perspective view illustrating retention of fluid in an inverted position.

Further with regard to FIG. 2A through FIG. 2D (and FIG. 5A through 5D), the device 20, 20a is shown in its closed position, or its in-use position. Also, the ring pivot 31 as defined herein is an inner ring 31. An outer ring 32 along with the inner ring 31 together define a flat top surface 33 of the receptacle 20, 20a in the in use position. Additionally with particular regard to FIG. 2D, a fluid capture area 34 is provided at the junction of the main body 20, 20a and the flange portion 30, so that when the receptacle 20, 20a is in the inverted position (FIG. 4), fluid 99 will be retained. The flange portion 30 is also provided with a slope 30 in the in-use position to help direct fluid properly to an interior of the main body 20, 20a.

FIG. 3A through FIG. 3G (also FIG. 5E and FIG. 5F) show the first 10 and second 10a preferred embodiments in the open position. By closer inspection, the flange portion 30 protrudes upward with respect to the main body portion 20, 20a, as opposed to the in-use position where the flange portion 30 protrudes inward. Also as shown in all the Figures and more particularly in FIG. 4, the device has a ring handle 40 at a lower end thereof, the ring handle providing for ease of removal using one finger of a user.

Many alterations and modifications may be made by those having ordinary skill in the art without departing from the spirit and scope of the invention. Therefore, it must be understood that the illustrated embodiments have been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

While the particular Device and Method for Menstrual Blood Collection as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

I claim:

1. A receptacle for collecting and retaining menstrual fluid, comprising:
    a main body;
    a flange portion that folds about a living hinge, the flange portion about the living hinge defining an open position and a closed position to the receptacle, the closed position further being an in use position, wherein further in the open position the flange portion protrudes upwardly and inwardly with respect to a spherical main body; and
    wherein a fluid capture area is provided at the junction of the main body and the flange portion so that when the receptacle is in an inverted position, fluid will be retained.

2. The receptacle for collecting and retaining menstrual fluid of claim 1, the flange portion further comprising a slope with respect to the main body, the slope acting like a funnel when the receptacle is in the in use position, directing fluid to an interior of the main body.

3. The receptacle for collecting and retaining menstrual fluid of claim 1, wherein when the receptacle is in an open position, the flange portion protrudes upward with respect to the main body portion, and wherein the receptacle is in a use position, the flange portion protrudes inward with respect to the main body.

4. The receptacle for collecting and retaining menstrual fluid of claim 1, further comprising a ring handle at a lower end thereof, the ring handle providing for ease of removal using one finger of a user.

5. A method for collecting menstrual fluid comprising:
    inserting a receptacle for collecting and retaining menstrual fluid, wherein the receptacle comprises;
    a main body;
    a flange portion that folds about a living hinge, the flange portion about the living hinge defining an open position and a closed position to the receptacle, the closed position further being an in use position, wherein further in the open position the flange portion protrudes upwardly and inwardly with respect to a spherical main body; and,
    wherein a fluid capture area is provided at the junction of the main body and the flange portions so that when the receptacle is in an inverted position, fluid will be retained in the fluid capture area; and,
    a ring handle providing a user ease of insertion and removal.

6. The method for collecting menstrual fluid of claim 5, wherein the receptacle is a first receptacle and further comprising:
    providing a second receptacle;
    changing the first receptacle for the second receptacle after a period of about six to twelve hours; and
    cleaning the first receptacle at a later time as compared to the step of changing the first receptacle.

7. The receptacle for collecting and retaining menstrual fluid of claim 1, wherein the fluid is retained in a catch area when the receptacle is removed by a user.

8. The receptacle for collecting and retaining menstrual fluid of claim 1, which is compressed during insertion and which has a resilience for restoring to the receptacle's original shape after being inserted into a vagina.

9. The receptacle for collecting and retaining menstrual fluid of claim 1, wherein the receptacle has a spherical, elliptical or egg shape.

10. The receptacle for collecting and retaining menstrual fluid of claim 4, wherein the ring handle provides for removal of the receptacle using one finger of a user.

11. The receptacle for collecting and retaining menstrual fluid of claim 1, wherein the receptacle is made from a soft compressible resilient elastomer material.

12. The method for collecting menstrual fluid of claim 5, wherein the fluid is retained in a catch area when the receptacle is removed by a user.

13. The method for collecting menstrual fluid of claim 5, wherein the receptacle for collecting and retaining menstrual fluid is compressed during insertion and which has a resilience for restoring to its original shape after being inserted into the vagina.

14. The method for collecting menstrual fluid of claim 5, wherein the receptacle for collecting and retaining menstrual fluid comprises a flange portion that folds about a living hinge, the flange portion about the living hinge defining an open position and a closed position to the receptacle, the closed position further being an in use position, wherein further in the open position the flange portion protrudes upwardly and inwardly with respect to the spherical main body.

15. The method for collecting menstrual fluid of claim 5, wherein the receptacle has spherical, elliptical or egg shape.

16. The method for collecting menstrual fluid of claim 5, wherein the ring handle provides for removal of the receptacle using one finger of a user.

17. The method for collecting menstrual fluid of claim 5, wherein the receptacle is made from a soft compressible resilient elastomer material.

* * * * *